United States Patent
Wapelhorst et al.

(10) Patent No.: US 10,309,941 B2
(45) Date of Patent: *Jun. 4, 2019

(54) GAS INLET SYSTEM FOR ISOTOPE RATIO ANALYZER AND METHOD OF DETERMINING AN ISOTOPE RATIO

(71) Applicant: Thermo Fisher Scientific (Bremen) GmbH, Bremen (DE)

(72) Inventors: Eric Wapelhorst, Bremen (DE); Hans-Jürgen Schlüter, Bremen (DE); Oliver Kracht, Bremen (DE); Johannes Schwieters, Bremen (DE); Michael Krummen, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/684,762

(22) Filed: Aug. 23, 2017

(65) Prior Publication Data

US 2017/0370890 A1 Dec. 28, 2017

Related U.S. Application Data

(63) Continuation of application No. 14/784,877, filed as application No. PCT/EP2014/057140 on Apr. 9, 2014, now Pat. No. 9,766,219.

(30) Foreign Application Priority Data

Apr. 15, 2013 (GB) .................... 1306806.9
Apr. 15, 2013 (GB) .................... 1306807.7
Apr. 15, 2013 (GB) .................... 1306808.5

(51) Int. Cl.
*G01N 33/00* (2006.01)
*G01N 21/31* (2006.01)
*H01J 49/04* (2006.01)

(52) U.S. Cl.
CPC ......... *G01N 33/0011* (2013.01); *G01N 21/31* (2013.01); *H01J 49/0422* (2013.01)

(58) Field of Classification Search
CPC .. G01N 21/31; G01N 33/0011; H01J 49/0422
(Continued)

(56) References Cited

U.S. PATENT DOCUMENTS

| 4,916,313 A | 4/1990 | Hall et al. |
| 5,424,539 A | 6/1995 | Brand et al. |

(Continued)

FOREIGN PATENT DOCUMENTS

| DE | 4421272 A1 | 1/1996 |
| EP | 0306333 A2 | 3/1989 |

(Continued)

OTHER PUBLICATIONS

Desage et al., "Gas chromatography with mass spectrometry or isotope-ratio mass spectrometry in studying the geographical origin of heroin," Anal. Chimica Acta, 247 (1991), pp. 249-254.

(Continued)

*Primary Examiner* — Harshad R Patel
(74) *Attorney, Agent, or Firm* — David A. Schell

(57) ABSTRACT

A gas inlet system for introducing gas into an isotope ratio analyzer, the gas inlet system including a reference system comprising: a first supply of a reference gas having a first known isotope ratio; a supply of a carrier gas, wherein the supplies of reference gas and carrier gas are each connected by respective reference and carrier gas lines to a first mixing junction where the reference gas and carrier gas combine; a mixing zone connected downstream of the first mixing junction wherein the combined reference gas and carrier gas mix together; an exit line for transporting the mixed gas from the mixing zone to the isotope ratio analyzer; and an opening on the exit line, wherein the opening is downstream of the mixing zone. Also provided is a method of determining an isotope ratio.

21 Claims, 8 Drawing Sheets

(58) Field of Classification Search
USPC .............................................. 73/202, 202.5
See application file for complete search history.

(56) References Cited

U.S. PATENT DOCUMENTS

| | | | |
|---|---|---|---|
| 7,928,369 | B2 | 4/2011 | Hatscher et al. |
| 8,222,596 | B2 * | 7/2012 | Tao .................. H01J 49/105 250/281 |
| 2009/0159795 | A1 | 6/2009 | Hatscher et al. |
| 2009/0314057 | A1 | 12/2009 | Hatscher et al. |
| 2011/0046896 | A1 | 2/2011 | Smajlovic |

FOREIGN PATENT DOCUMENTS

| | | |
|---|---|---|
| JP | 01-127955 A | 5/1989 |
| JP | 2006-64484 A | 3/2006 |
| JP | 2009-531677 A | 9/2009 |
| WO | 97/23779 A1 | 7/1997 |
| WO | 02/25250 A2 | 3/2002 |
| WO | 2007/057527 A1 | 5/2007 |

OTHER PUBLICATIONS

Hall et al., "Routine analysis by high precision gas chromatography/mass selective detector/isotope ratio mass spectrometry to 0.1 pats per mil," Rapid Communications in Mass Spectrometry (1999), 13, pp. 1231-1236.

Hayes et al., "Compound-specific isotopic analyses: A novel tool for reconstruction of ancient biogeochemical processes," Organic Geochemistry, 1990, vol. 16, No. 4-6, pp. 1115-1128.

Morrison et al., "A streamlined approach to the analysis of volatile fatty acids and its adaptation to the measurement of whole-body flux," Rapid Communications in Mass Spectrometry, 2004 (18), pp. 2593-2600.

Nitz et al., "Multidimensional gas chromatography—isotope ratio mass spectrometry (MDGC-IRMS). Part A: System description and technical requirements," J of High Resolution Chromatography, (1992), vol. 15 (6), pp. 387-391.

Schauer et al., "An automated system for stable isotope and concentration analyses of CO2 from small atmospheric samples," Rapid Communications in Mass Spectrometry, 2005, vol. 19, (3), pp. 359-362.

Schmitt et al., "Amount-dependent isotopic fractionation during compound-specific isotope analysis," Rapid Communications in Mass Spectrometry, 2003, vol. 17 (9), pp. 970-977.

Tuzson, et al., "High precision and continuous field measurements of δ13C and δ18O in carbon dioxide with a cryogen-free QCLAS", Appl. Phys. B 92 (2008), 451-458.

Werner, et al., "Referencing strategies and techniques in stable isotope ratio analysis," Rapid Communications in Mass Spectrometry, 2001, vol. 15 (7), pp. 501-519.

* cited by examiner

GAS INLET SYSTEM FOR ISOTOPE RATIO ANALYZER AND METHOD OF DETERMINING AN ISOTOPE RATIO

CROSS-REFERENCE TO RELATED APPLICATIONS

The present application is a continuation under 35 U.S.C. § 120 and claims the priority benefit of co-pending U.S. patent application Ser. No. 14/784,877 filed Oct. 15, 2015, which is a National Stage application under 35 U.S.C. § 371 of PCT Application No. PCT/EP2014/057140, filed Apr. 9, 2014. The disclosures of each of the foregoing applications are incorporated herein by reference.

FIELD

This disclosure generally relates to gas inlet systems for isotope ratio analyzers, to said analyzers incorporating said inlet systems and to methods of isotope ratio measurement.

BACKGROUND

Isotope-ratio analysis is used to measure the relative abundance of isotopes (isotope ratio) in a gaseous sample. For instance, it is used for determining the isotope ratios $^{13}C/^{12}C$ and/or $^{18}O/^{16}O$ from $CO_2$ e.g. in air. Isotope-ratio analysis is most commonly performed by mass spectrometry (MS) but may also be performed by optical spectrometry.

Gas inlet systems for isotope ratio analysis are well known, especially for use with isotope ratio mass spectrometers. A general review of isotope ratio mass spectrometry and gas inlet systems can be found in Brenna et al, Mass Spectrometry Reviews, 1997, 16, 227-258. Isotope-ratio mass spectrometry usually comprises comparative measurements of isotope ratios of a sample gas and of one or more reference gases of known isotope ratio. Accordingly, isotope ratio MS (IRMS) typically requires at least one sample gas inlet and at least one reference gas inlet.

A popular solution for gas flow management is the so called open split, which comprises a mixing region that is open to the atmosphere. Gases to be analyzed emerge from a line into the mixing region and whilst a large proportion of the gases is lost to the atmosphere as excess a small amount is transferred to a further line. The open split thus vents gas flow in excess of that acceptable by the isotope ratio analyzer. In isotope ratio MS an example of an open split design is known from U.S. Pat. No. 5,424,539, wherein the open split comprises a small glass vial open to the atmosphere with various sample, reference and carrier gas capillaries ending in the vial and a further capillary sampling the mixing region within the vial. The carrier gas is used to dilute the various sample and reference gases to achieve a desired concentration for analysis. However, the design is not as robust as would be desired and excess sample gas is lost from the system in the open split prior to analysis. A significant amount of carrier gas also has to be used. A similar open split design is described in U.S. Pat. No. 5,661,038 and shown in Tobias et al, Anal. Chem. 1996, 68, 3002-3007. The open split concept has been refined for improved performance and automation, for example as shown in U.S. Pat. No. 7,928,369 and WO 2007/112876, wherein the capillaries for supplying gases are provided with drives for movement in and out of the mixing zone. In all, such open splits as described, essentially comprising an array of nested capillaries, are not simple to manufacture and can lack reproducibility in production as well as robustness in use.

A type of open split is used in gas chromatography MS (GCMS) for pressure adaption, although it is not used in isotope ratio MS. Such an open split is the Open-Split Capillary Interface Part No. 113532 from SGE (www.sge-.com).

Gas inlet systems configured for autodilution of samples using an open split are also known in the form of the Thermo Scientific GASBENCH and Thermo Scientific CONFLO interfaces for isotope ratio MS (www.thermoscientific.com).

As mentioned above, isotope ratio MS (IRMS) typically requires at least one sample gas inlet and at least one reference gas inlet. The attained measurement precision is typically about 0.05% and accuracy is derived from that precision by use of the reference gas. However, in isotope ratio optical spectrometry (IROS) there is not currently offered an equivalent effective solution for reference and calibration. A system for calibrating the isotope ratio measurements to account for concentration dependence and a delta scale contraction is described in B. Tuzson et al, *High precision and continuous field measurements of $\delta^{13}C$ and $\delta^{18}O$ in carbon dioxide with a cryogen-free QCLAS*, Appl. Phys. B (2008), Volume 92, pp 451-458. However, a drawback with the system described in Tuzson et al is that it utilizes a significant number of separate diluted supplies of reference gases of known isotope ratio. Such reference gas/air mixtures are not commonly available when working in the field for example. Furthermore, the system described Tuzson et al does not employ a sample dilution.

Isotope ratio optical spectrometers differ in several aspects from isotope ratio mass spectrometers: IROS requires a higher inflow of sample; an IROS system overall is more compact, which makes it transportable, but which in turn requires extra ruggedness, and this also applies to the gas inlet system; the IROS market is more price sensitive, necessitating simple low-cost solutions. As a consequence, conventional IRMS gas inlet systems are not first choice for use as IROS inlet systems; and a cheaper, more compact and simpler system designed for higher flow rates is required for IROS measurements.

From this background it can be seen that it would be desirable to provide a gas inlet system for an isotope ratio analyzer that is compact and robust, easy and cheap to manufacture, and furthermore allows comparative measurement of isotope ratios of a sample and one or more reference gases. It would also be desirable in an inlet system to reduce the loss of excess sample gas that occurs with conventional open split configurations.

The disclosure has been made against this background in order to try to alleviate one or more of the aforementioned problems as well provide one or more additional advantages as hereafter described.

SUMMARY

According to a first aspect, there is provided a gas inlet system for introducing gas into an isotope ratio analyzer, comprising:
  a supply of analyte gas;
  an analyte gas line for transporting a flow of analyte gas from the supply of analyte gas;
  a supply of carrier gas; and
  a carrier gas line for transporting a flow of carrier gas from the supply of carrier gas;

wherein the analyte gas line joins the carrier gas line at an analyte-carrier junction to mix the analyte gas and the carrier gas, wherein the junction is further connected to an exit line for transporting the mixed gas from the junction to the isotope ratio analyzer, and wherein the junction is positioned downstream of an opening on the carrier gas line. The junction and the opening on the carrier gas line are arranged whereby when the flow rate of the analyte gas in the analyte line is arranged to be lower than the flow rate of gas into the isotope ratio analyzer the flow between the opening and the analyte-carrier junction is always towards the isotope ratio analyzer, and whereby when the flow rate of the analyte gas in the analyte line is arranged to be higher than the flow rate of gas into the isotope ratio analyzer the flow between the opening and the analyte-carrier junction is always towards the opening. Accordingly, the gas inlet system can be configured in one mode of operation such that the flow rate of the analyte gas in the analyte line is lower than the flow rate of gas into the isotope ratio analyzer. Accordingly, the gas inlet system may be configured in another mode of operation such that the flow rate of the analyte gas in the analyte line is higher than the flow rate of gas into the isotope ratio analyzer. In various embodiments, the gas inlet system can be configured such that the flow rate of the analyte gas in the analyte line is not substantially identical to the flow rate of gas into the isotope ratio analyzer.

Also provided is an isotope ratio analyzer comprising the gas inlet system according to the first aspect.

Diffusion of the analyte gas backwards, i.e. upstream, to the opening is restricted by the magnitudes of the flow rates and the distance from the analyte-carrier junction to the opening. The first aspect thus provides a substantially complete analyte gas transfer from the analyte gas supply into the isotope ratio analyzer, i.e. with substantially no loss of analyte gas through the opening, which instead carries away only excess carrier gas, such as to the atmosphere. The carrier gas is typically less valuable (usually cheaper) than the analyte gas and therefore it can afford to be wasted more. In other words, the analyte-carrier junction and the opening and the distance between are configured such that when the flow rate of the analyte gas in the analyte line is arranged to be lower than the flow rate of gas into the isotope ratio analyzer the flow between the opening and the analyte-carrier junction is always towards the isotope ratio analyzer.

In various embodiments, the system can comprise a supply of analyte gas to supply analyte gas to the analyte gas line. The analyte gas may be a sample gas (e.g. of unknown isotope ratio and/or unknown concentration, which are to be measured) or a reference gas (e.g. of known isotope ratio for calibration of the analyzer). In various embodiments, the analyte gas is a sample gas. The system also comprises a supply of carrier gas to supply carrier gas to the carrier gas line. The carrier gas supply can be substantially free from the analyte gas. An embodiment is wherein the analyte gas is $CO_2$ and the carrier gas is a gas substantially free from $CO_2$, e.g. $CO_2$-free air or $CO_2$-free nitrogen ($N_2$). The analyte and carrier gas lines respectively transport the flow of analyte and carrier gas from their supplies towards the analyzer. In some embodiments there may be more than one analyte gas supply and/or more than one analyte gas line. In some embodiments there may be more than one carrier gas supply and/or more than one carrier gas line.

According to a second aspect, there is provided a gas inlet system for introducing gas into an isotope ratio analyzer, the gas inlet system including a reference system comprising:

at least a first supply of a reference gas having a first known isotope ratio;

a supply of a carrier gas (such as the same supply of a carrier gas as may supply the carrier gas line in the first aspect), the carrier gas can be being free of reference gas;

wherein the supplies of reference gas and carrier gas are each connected by respective reference and carrier gas lines to a first mixing junction where the reference gas and carrier gas combine, such as wherein the carrier gas flow to the first mixing junction is controllable by flow control means;

a mixing zone connected downstream of the first mixing junction wherein the combined reference gas and carrier gas mix together;

an exit line for transporting the mixed gas from the mixing zone to the isotope ratio analyzer; and an opening on the exit line, wherein the opening is downstream of the mixing zone.

The reference (also termed calibration) system can further comprise at least a second supply of a reference gas having a second known isotope ratio. In various embodiments, the chemical composition of the first and second reference gas is the same (e.g. both may be $CO_2$) and they differ only in the isotope ratio. The first and second supplies of reference gas may each be independently (e.g. alternately or not simultaneously) connected to the first mixing junction for mixing with the carrier gas as required. The first mixing junction can be a T-junction. Herein the term T-junction means any junction of three flow channels, i.e. it has three arms. It may be provided as a T-piece, or Y-piece, or a junction of three orthogonal channels, and may be either two-dimensional wherein the three channels lie in the same plane or three dimensional (e.g. in the form of a three-dimensional "tripod" configuration) wherein the three channels do not all lie in the same plane. Herein, a mixing junction where two gases meet and are mixed can be not open to the atmosphere, in contrast to prior art systems where mixing occurs at open splits. This enables the critical flows for mixing to be under full control.

The opening can be open to atmosphere. The opening to atmosphere ensures that the flow in the exit line does not exceed that which can be handled by the isotope ratio analyzer. The opening can be in the form of an open capillary. The opening can be situated on a junction (opening junction), such as a T-junction, positioned downstream of the mixing zone. This opening should not offer a marked restriction to the gas flow so that the pressure at the junction with the opening is always very close to the atmospheric pressure. This means that the flow rates through this opening will not be too high. The pressure drop across the opening can be arranged to be 250 mbar or less, especially 50 mbar or less. On the other hand, the flow rate through this opening should be high enough to make sure that back-diffusion of the reference gas against the carrier gas flow is small enough; otherwise this would lead to fractionation (altering of the isotope ratio). As an example, the opening in the form of an open capillary may be at least 0.5 mm, e.g. 0.5 mm to 2 mm, in internal diameter and can be at least 5 mm, or at least 10 mm in length. An exemplary flow rate to the junction with such open capillary can be at least 1 ml/min and an exemplary flow rate through such open capillary can be at least 0.5 ml/min. The loss of flow through the open split is then typically $<1/1000$ of input flow.

The mixing zone, which typically comprises a length of capillary between the first mixing junction and the opening junction, may be a straight capillary but can include one or more bends and/or includes an angle between the two junctions (e.g. 90 degrees). Mixing within the mixing zone may be increased in this way. In addition or alternatively, the mixing zone may comprise one or more changes of internal diameter (internal cross section area). Other means to improve mixing in the mixing zone include: use of carrier gas with high interdiffusion coefficient, heating the mixing zone, modifying the junctions so that the addition of the reference gas is in the middle of the cross section of the mixing zone capillary, bends in the mixing zone and/or the use of baffles or other mixing devices (passive or active).

The flow control means to control carrier gas flow to the first mixing junction enables controlled dilution of the reference gas so that measurements of isotope ratio of the reference gas may be made by the analyzer at a plurality of different concentrations. The flow control means enables the carrier gas flow to be regulated or dynamically controlled, e.g. wherein the flow control means comprises a mass flow controller or proportional valve. The flow control means may be any flow controller or regulated valve. The flow control means may be, for example, a mass flow controller or proportional valve, or volume flow controller, or a switchable combination of fixed flow restrictions allowing the flow to be adjusted in discrete steps as described in U.S. Pat. No. 7,928,369 and WO 2007/112876. The flow control means may be automatically or manually operated. The flow control means may comprise at least one automatic or manual pressure regulator combined with at least one flow restriction downstream of the pressure regulator. The flow control means may be an automatic, electronic or digital flow controller, for example as described in WO 2007/112876. One example of a flow control means is the CONFLOIV from THERMO SCIENTIFIC.

The calibration system can comprise two stages of dilution of the reference gas with the carrier gas. In various embodiments, only one of the dilution stages has the flow of carrier gas dynamically regulated, e.g. by mass flow controller. In particular embodiments, the first stage of dilution has the flow of carrier gas dynamically regulated. In various embodiments, the calibration system further comprises a second mixing junction on the exit line from the mixing zone wherein further carrier gas can be mixed with the already mixed gas. In this case, the gas emerging from the mixing zone after a first stage of dilution is a pre-mixture of reference gas and carrier gas, which is further diluted with additional carrier gas in the second stage of dilution. The second mixing junction can be downstream of the opening on the exit line. The carrier gas supplied to the second mixing junction can be from the same supply of carrier gas that supplies the first mixing junction, i.e. there can be only one supply of carrier gas. The same supply of carrier gas can also be to supply the carrier gas in the first aspect. The carrier gas can be transported to the second mixing junction by a second carrier gas line. The carrier gas supplied to the second mixing junction can be not regulated or dynamically controlled, i.e. a mass flow controller or proportional valve is not used in that case. Thus, dilution of the reference gas can be regulated by the control of carrier gas flow to the first mixing junction. In some embodiments it may be possible to regulate dilution of the reference gas by dynamic control of the carrier gas flow to the second mixing junction instead of to the first mixing junction.

The exit line from the mixing zone can have a flow restriction upstream of the second mixing junction, but can be situated downstream of the opening junction. The second carrier gas line can also have a flow restriction upstream of the second mixing junction. These two flow restrictions ensure a flow ratio between the flow of the pre-mixture and the flow of the carrier at the second mixing junction. The flow ratio (pre-mixture:carrier) may be for example about 1:30. In the case of a $CO_2$ reference gas, the $CO_2$ concentration of the pre-mixture can be in the range from about 13,000 ppm down to 4,000 ppm (parts per million). In the diluted gas that enters the analyzer (i.e. after second dilution where a second dilution is used) the $CO_2$ concentration can be in the range between about 200-4000 ppm, such as 200-3,500 ppm ($CO_2$ in air or $CO_2$ in nitrogen concentration), with the range between about 200-1500 ppm being more optimal. This is optimized for measuring ambient $CO_2$, which is typically at least 400 ppm. These concentration ranges are especially applicable for a measurement cell of an analyzer that is a laser cell for performing laser absorption measurements on the gas. These concentration ranges may also apply to some other analyte gases, optionally with some variation. For gases other than $CO_2$, e.g. methane, it is desirable to adjust the system for the optimum concentration of the gas to be measured. In general, the concentration of gas that enters the analyzer can depend on the application and factors such as the type of analyte gas, the strengths of absorption lines, and the sensitivity of the analyzer.

In various embodiments, the supply of reference gas that is supplied to the apparatus or used for the method is a pure gas, or is diluted by a factor not more than about 2, or not more than about 5, or not more than about 10.

The disclosure thus provides a system capable of allowing determination of a concentration dependence of the isotope ratio measurement (linearity calibration), especially relevant for isotope ratio optical spectrometry. In further embodiments, it can further provide determination of an isotope ratio dependence of the isotope ratio measurement (delta scale contraction).

According to a third aspect there is provided a method of determining an isotope ratio, comprising:
 providing a reference gas at a first known isotope ratio;
 measuring the isotope ratio of the reference gas with the first known isotope ratio at a plurality of concentrations in a carrier gas;
 determining a concentration dependence of the isotope ratio measurements of the reference gas with the first known isotope ratio;
 providing a sample gas of unknown isotope ratio and unknown concentration;
 measuring the isotope ratio and concentration of the sample gas; and
 correcting the measured isotope ratio of the sample gas by the determined concentration dependence.

In an embodiment, the method further comprises:
 providing the reference gas at a second known isotope ratio;
 measuring the isotope ratio of the reference gas with the second known isotope ratio, such as at one or more concentrations in the carrier gas that lie within the range of measured concentrations of the reference gas with the first known isotope;
 determining an isotope ratio calibration from the measured isotope ratios of the reference gas with the first and second known isotope ratios; and
 further correcting the measured isotope ratio of the sample gas by the determined isotope ratio calibration.

In various embodiments, the sample gas is also diluted in the carrier gas prior to measuring the isotope ratio. In various embodiments, the sample gas is also diluted to a concentration in the carrier gas that lies within the range of concentrations of the reference gas with the first known isotope. The sample gas may be diluted using the system according to the first aspect. In some cases, the sample gas may not be diluted in the carrier gas prior to measuring the isotope ratio, i.e. it may be used as supplied.

The sample gas may have a range of concentrations. The reference gas can be diluted to at least a concentration in the carrier gas that lies within the range of concentrations of the sample gas.

The reference gas can be provided as a substantially pure gas and the carrier gas can be provided as substantially free from the reference gas. Where the analysis is of $CO_2$, the reference gas is $CO_2$ and the isotope ratio can be the ratio $^{13}C/^{12}C$ or $^{18}O/^{16}O$, especially $^{13}C/^{12}C$. The carrier gas therefore can be a $CO_2$-free gas such as $CO_2$-free air or $CO_2$-free $N_2$. The sample gas therefore will also comprise $CO_2$ to be measured. Other gases that may be measured for their isotope ratios and therefore used as a reference include, for example: $CH_4$, $C_2H_6$, $C_xH_{(2x+2)}$ where x=integer, water vapor (e.g. in ambient air), CO, small hydrocarbons, alcohols, aldehydes, $NO_x$, $N_xO_y$ where x=1, 2 and y=1, 2, 3, 4 or 5 (e.g. NO, $NO_2$ or $N_2O$), $H_2S$, nitrogen, oxygen, or hydrogen, or other gases.

A list of some examples of analyte gases and some of their measurable isotope ratios is given below.

| Gas | Isotope ratio | | | |
|---|---|---|---|---|
| $CO_2$, CO: | $^{13}C/^{12}C$ | $^{18}O/^{16}O$ | $^{17}O/^{16}O$ | |
| $CH_4$, other alkanes: | $^{13}C/^{12}C$ | $^{2}H/^{1}H$ | | |
| $N_2O$: | $\alpha$-$^{15}N/^{14}N$ | $\beta$-$^{15}N/^{14}N$ | $^{18}O/^{16}O$ | $^{17}O/^{16}O$ |
| $N_xO_y$: | $^{15}N/^{14}N$ | $^{18}O/^{16}O$ | $^{17}O/^{16}O$ | |

The carrier gas may be selected from: air, nitrogen, helium or argon, or mixtures of any two or more of the foregoing.

Advantageously, a single supply of reference gas with the first known isotope ratio can be employed, which is dynamically diluted with carrier gas to provide the plurality of concentrations used for measuring the isotope ratio and determining the concentration dependence of the isotope ratio. This removes the need for a plurality of prepared reference gases at different known concentrations.

In various embodiments, the dilution of reference gas comprises two stages of dilution, for example in the manner of the calibration system described.

In various embodiments, the supply of reference gas that is supplied to the apparatus or used for the method is a pure gas, or is diluted by a factor not more than about 2, or not more than about 5, or not more than about 10. Such supply of reference gas can then be subjected to the mentioned dynamic dilution, especially by the mentioned two stages of dilution.

In various embodiments, the measurements of the isotope ratio of the reference and sample gas are made using an optical spectrometer, but may be made using a mass spectrometer, or other spectrometer or measurement device.

The method of the third aspect may be performed using the systems of the first and second aspects.

The flow of the carrier gas in the third aspect can be at least partially regulated or dynamically controlled by the flow control means. The flow control means can comprise a mass flow controller or proportional valve, which can further be computer controlled (i.e. under the control of software). In this way, the dilution of the reference gas can be controlled. The dilution of reference gas comprises two stages of dilution with carrier gas. In various embodiments, a flow of the carrier gas in a first stage of dilution of the reference gas is dynamically controlled by flow control means. In various embodiments, a flow of the carrier gas in a second stage of dilution is not dynamically controlled.

In various embodiments, the method further comprises connecting the reference gas and carrier gas by respective reference and carrier gas lines to a first mixing junction where the reference gas and carrier gas combine; mixing the combined reference gas and carrier gas in a mixing zone downstream of the first mixing junction; transporting the mixed gas from the mixing zone to the isotope ratio analyzer along an exit line; and providing an opening to atmosphere on the exit line downstream of the mixing zone.

In various embodiments, the sample gas is diluted with the carrier gas at a junction, wherein the junction is further connected to an exit line for transporting the mixed gas from the junction to the isotope ratio analyzer, and wherein the junction is positioned downstream of an opening to atmosphere on a carrier gas line, whereby the flow rate of the analyte gas to the junction is arranged to be lower than the flow rate of gas into the isotope ratio analyzer whereby the flow between the opening and the junction is always towards the isotope ratio analyzer.

Features and further details will now be described.

The sample gas and/or reference gas can be $CO_2$. The isotope ratio to be measured for the sample gas and the reference gas thus can be $^{13}C/^{12}C$ and/or $^{18}O/^{16}O$. The reference gas can be a pure gas, e.g. pure $CO_2$. This compares to the use of reference gases pre-diluted at a known concentration in prior art calibration systems. The dilution from a pure gas source enables complete flexibility in setting the concentration of the gas admitted to the analyzer. Advantageously, a commercial-size (e.g. 10 liter of $CO_2$) bottle of pure reference gas, which can be diluted with the carrier gas, can last a very long time, in some cases perhaps for the working lifetime of the analyzer. Thus, changing bottles of reference gas can be hardly ever required. The carrier gas can conversely be reference gas-free, e.g. for CO reference gas, the carrier can be a $CO_2$-free gas, e.g. $CO_2$-free air or $CO_2$-free $N_2$. Advantageously, such carrier gas can be generated in the field.

Herein the term gas line refers to any channel, conduit, tube, capillary or the like for transporting gas. Situated on a line may be any number of devices, for example devices such as junctions, valves, flow restrictions, flow controllers, gauges and the like.

The junctions mentioned herein can be T-junctions as defined above and/or can be one or more junctions and one or more portions of the gas lines are provided in a machined block, i.e. in one mechanical piece. In other words, manufacturing of at least part of the system can be by machining out of a bulk material (e.g. a metal block), which allows better reproducibility in production. Such construction provides improved rigidity to the system and allows integration of the opening (open split) and other parts of the gas inlet into one mechanical piece. Using T-junction configurations at the junctions with openings, with or without manufacture in a machined block, ensures that the critical flows through the openings are under full mechanical control (in the prior art the open split was conventionally provided as an array of nested tubes in an open vial), which in turn allows control over the mathematics of the flow and management of fractionation processes at such 'open splits'. The T-junction design enables well separated diffusion paths, which facilitates calculating the system because the flow properties are well determined In another aspect, the present disclosure provides a gas inlet system for an isotope ratio analyzer comprising: at least a supply of each of a reference gas, a sample gas and a carrier gas for diluting the reference gas or sample gas, one or more T-junctions for allowing the carrier gas to dilute the reference gas or sample gas, and one or more separate T-junctions having an opening to atmosphere (i.e. one of the arms of the T-junction opens to atmosphere).

In a further aspect, the present disclosure provides a gas inlet system for an isotope ratio analyzer, comprising: at least a supply of each of a reference gas, a sample gas and a carrier gas for diluting the reference gas or sample gas, one or more junctions for allowing the carrier gas to dilute the reference gas or sample gas, and one or more junctions having an opening to atmosphere, wherein at least some gas flow channels for the gases (and/or the junctions) are provided as machined channels in a mechanical block. The one or more junctions having an opening to atmosphere are separate to the one or more junctions allowing the carrier gas to dilute the reference gas or sample gas. Where the gas flow channels extend outside of the mechanical block they can be provided as capillaries, e.g. fused silica, or metal, or polymer (e.g. PEEK) capillaries.

Thus the gas inlet system of the present disclosure is one which can be provided in a compact and robust form, especially where junctions between gas lines are provided as T-junctions, compared to the prior art open splits where the junction between flows, especially for dilution purposes, is provided in the form of an open vial. Providing at least part of the gas lines in a machined block is another advantage for system robustness and reproducibility in manufacture.

Using the present disclosure, the concentration of the sample gas and reference gas can be matched to one another and to the optimum concentration range suitable for the isotope ratio analyzer used.

The disclosure also provides numerous improvements to so-called open splits for isotope ratio analyzer gas inlets, especially for isotope ratio optical spectrometers. Further advantages of the disclosure include that arranging an opening on a carrier (dilution) gas line upstream of where a sample gas line joins the carrier gas line can provide for little or no sample loss, and an addition of only a minimum of carrier gas. In addition, an open split can be configured such that only a minimum of a reference or sample gas is split away from the flow into the isotope ratio analyzer.

The gas inlet system can also be used with an isotope ratio analyzer for concentration measurements and a calibration (linearity calibration) for the concentration dependence of isotope ratio measurements can be determined and used for correction of sample measurements.

The isotope ratio analyzer may be any type of analyzer capable of measuring an isotope ratio, especially an isotope ratio mass spectrometer or an isotope ratio optical spectrometer but embodiments are particularly advantageous in the case of an isotope ratio optical spectrometer (i.e. optical absorption spectrometer), especially a laser spectrometer (i.e. laser absorption spectrometer). Such spectrometers typically operate in the infrared region, such as the mid-infrared region (e.g. 2.5 µm-6 µm). Accordingly, the isotope ratio analyzer can be an isotope ratio optical spectrometer, moreover can comprise a measurement cell for performing optical absorption measurements on the gas to be analyzed. In various embodiments, the measurement cell is a laser cell for performing laser absorption measurements on the gas to be analyzed. The laser cell can be a multi-pass cell. The optical pathlength in the cell provided by the sum of the multiple laser passes may be in the ranges 1 to $10^5$ m, or 1 to $10^4$ m, 1 to $10^3$ m or 1 to $10^2$ m, or 1 to 10 m. A single measurement cell can be employed for measurement of both reference and sample gases. Such laser cell is typically pumped by a pump on the outlet from the cell. A laser measurement cell can satisfy the inequality $I*L*C < 1.6*10^{-12}$, where:
I=Spectral intensity in cm
L=length of the optical path in cm
C=Concentration of the measured gas in ppm.

The isotope ratio is generally determined in such an analyzer by measuring two (or more) separate spectral absorption lines, typically in the infrared region, at least one line for each different isotopic species (isotopologue), e.g. a line for $^{12}C^{16}O_2$ and another line for $^{13}C^{16}O_2$. An absorption line for $CO_2$ can be the line at or about 4.329 µm. The ratio of the intensities of the spectral absorption lines is a measure of the ratio of the abundance of each of the isotopic species (and hence the isotope ratio $^{13}C/^{12}C$ in this case (which can be expressed as the established delta notation, $\delta^{13}C$)). In general, the isotope ratios herein can be expressed as the established delta notation ($\delta$).

The isotope ratio analyzer may be configured for measuring the isotope ratio $^{13}C/^{12}C$ and/or $^{18}O/^{16}O$ from $CO_2$. It will be appreciated that it is also suitable for measuring other isotope ratios such as H/D in $CH_4$ analysis as well as referencing isotope ratios (e.g. $^{13}C/^{12}C$ or $^{18}O/^{16}O$ or $^{15}N/^{14}N$) in other gases such as $N_2O$ or CO for example. The types of other gases and their isotope ratios that can be analyzed by embodiments of the present disclosure are not particularly limited and further examples are described elsewhere herein. It will be appreciated that for other gases, a suitable adjustment of the gas concentration and flow rate may be required depending on the nature of the measurement and the sensitivity of the analyzer. Herein, measuring the isotope ratio $^{13}C/^{12}C$ and/or $^{18}O/^{16}O$ (or other isotope ratio) may comprise determining the ratio specifically or a quantity representative of the ratio (e.g. the delta value).

The above features are further described below, along with other details of the disclosure, with reference to the Figures.

LIST OF FIGURES

DETAILED DESCRIPTION OF EMBODIMENTS

In order to assist further understanding, but without limiting the scope thereof, various exemplary embodiments are now described with reference to the Figures.

Figure 1:
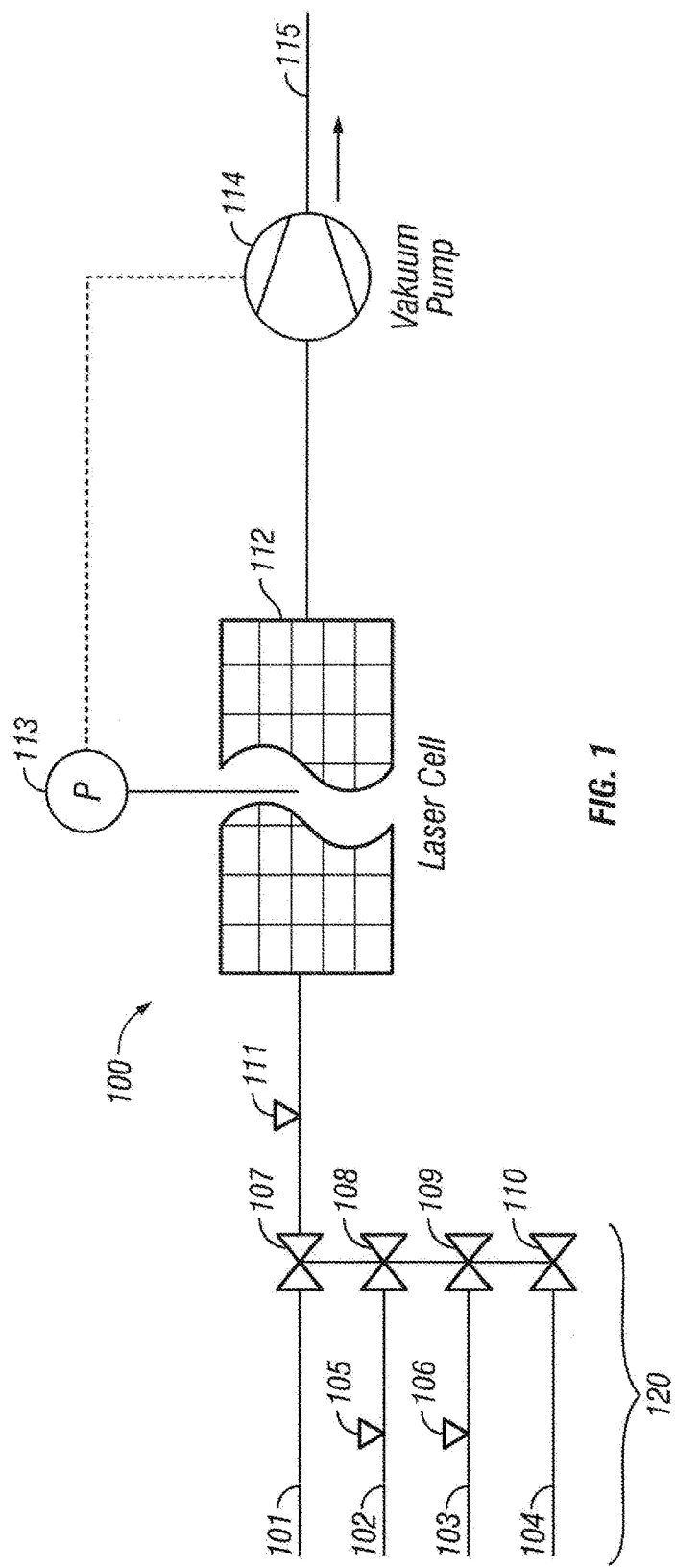
FIG. 1 shows a schematic layout of an isotope ratio optical spectrometer interfaced to a gas inlet system in accordance with the present disclosure.

Referring to FIG. 1, there is shown schematically an isotope ratio optical spectrometer (100) interfaced to a gas inlet system (120) in accordance with the present disclosure. It will be appreciated that the isotope ratio optical spectrometer could in other embodiments be replaced with an isotope ratio mass spectrometer interfaced to the gas inlet system. The optical spectrometer is a laser spectrometer. A sample (or reference) gas to be measured is transported from the gas inlet system (120) through a multi-pass measurement cell (112) in the laser spectrometer by a vacuum pump (114), such as a membrane pump, in the outlet (115) from the spectrometer that pumps the cell. The measurement cell has a total optical pathlength of approximately 5.4 m. The incoming gas is directly and completely transferred into the measurement cell (112). A filter (not shown) upstream of the cell prevents transfer of particles into the cell. The inlet flow into the measurement cell in this embodiment is limited by a fixed flow restriction (111) and is set to allow a gas flow rate of 80 ml/min into the cell for atmospheric pressure at the inlet ports (101, 104) and 0.5 bar(g) at inlet ports (102, 103). The actual flow through the measurement cell however depends on the pressure of the delivered gas. The pressure in the measurement cell (112) is kept constant by controlling the pump speed, for example in this embodiment by feedback to the pump (114) of signals generated from a pressure gauge (113) connected to the cell (112). It is also possible in other embodiments to have an adjustable valve between cell (112) and pump (114) and control the valve instead of the pump (114), e.g. using the feedback from pressure gauge (113). In this way, the pressure in the cell is desirably maintained generally in the range 20-200 mbar(a), such as 40-200 mbar(a), even 40-150 mbar(a). The pressure in the measurement cell is typically kept constant at approximately 100 mbar(a) (or in the range 20 to 150 mbar(a), or even to 200 mbar(a)). The operating measurement range of the cell is 200-4,000, such as 200-3,500, ppm of $CO_2$ in air or in $N_2$ with highest performance of detection between 200-1,500 ppm, especially 300-1,500 ppm of $CO_2$.

An isotope ratio is generally determined in the measurement cell by measuring two separate spectral absorption lines, typically in the infrared region, one line for each different isotopic species (isotopologue), e.g. an absorption line for $^{12}C^{16}O_2$ and another line for $^{13}C^{16}O_2$. A convenient absorption line for $CO_2$ is the line at or about 4.3218 μm. If more lines are available per isotope (e.g. a doublet or triplet) it is possible to measure and use the information from more than one line, e.g. for other gases than $CO_2$ or in other spectral ranges that might be interesting. The ratio of the intensities of the spectral absorption lines is a measure of the ratio of the abundance of each of the isotopic species (and hence the isotope ratio, e.g. $^{13}C/^{12}C$). The outputs of the spectrometer are thus ratios of different isotopic lines (e.g. $R_{13C=C13c/C12c}$). The result is referenced against international standards using the established delta notation for isotope ratio reporting (e.g. $\delta^{13}C$ [‰]). The means for performing calibrations, which are required to calculate a δ-value from a ratio of spectral intensities, are described below.

On the gas inlet line into the measurement cell a multiport valve (shown schematically as distinct valves 107-110 for illustration purposes) allows switching between four different gas inlet ports (101-104). One of these ports (101) is connected to a gas inlet and referencing system according to the disclosure as described in more detail below (see FIG. 2). The remaining ports (102-104) can optionally be used, for example, for additional sample gas (e.g. ambient air at port 104) and/or calibration gases for additional concentration calibration (102, 103). The latter requires one or two references with known concentration. The inlet and referencing system connected to port (101) is typically used for calibration of the concentration dependence of the isotope ratio measurement and for the isotope ratio dependence of the isotope ratio measurement as described below.

The apparatus and method of the disclosure is illustrated in the embodiments below with the example of a $CO_2$ analysis system (i.e. $CO_2$ as sample and reference gas) but it should be appreciated that the disclosure is applicable to any other gas that is susceptible to isotope ratio analysis, either by optical spectrometry or mass spectrometry or other spectrometry technique. In those cases, the reference gas will not be $CO_2$ but will the same gas as the particular sample gas being analyzed. Similarly, the apparatus and method is illustrated in the embodiments below with the example of an optical spectrometer but it should be appreciated that the disclosure is applicable to a mass spectrometer or other spectrometer.

It has been found that the isotope ratio reported by the spectrometer differs with gas concentration and therefore a correction factor (also termed linearity calibration or concentration dependence) that depends on the $CO_2$ concentration is required for each ratio. To calculate these linearity calibration factors, the spectrometer needs to measure $CO_2$ with the same isotopic ratio at different concentration, or at least numerous reference gases with known isotopic ratio and concentration are needed.

In addition, it is known that there is an isotope ratio dependence of the isotope ratio measurement (the so-called delta scale contraction). Typically (at least) two reference gases of known and different isotope ratio are necessary to calculate the delta scale contraction. The highest accuracy is achieved if the reference gases used for the delta scale contraction have a similar concentration to that of the measured sample(s) and their delta values narrowly frame the delta value(s) of the sample(s). Therefore the two references gases should be diluted to give a $CO_2$ gas concentration in the range 100-4,000 ppm $CO_2$ in air, which is the operating measurement range of the spectrometer, such as 200-4,000 ppm, even 200-3,500 ppm, and optimally 400-2,000 ppm $CO_2$ in air. For each different type of gas, there can be a range of gas concentrations in the analyzer with a width of approximately 1 decade for the given analyzer configuration (e.g. optical path, and analyzer sensitivity). The position of this range can be adjusted by changes to the configuration. Thus, for each gas the requirement is to match the concentration of the gas reaching the analyzer with the dynamic range of the analyzer.

Regular referencing and calibration of the spectrometer ensures high data quality and accurate analysis. This regular referencing and calibration is facilitated by the referencing system of the gas inlet as described below.

For linearity calibration and delta scale contraction, mixtures of reference $CO_2$ with carrier gas, using $CO_2$ from two different sources (with different known isotope ratios), are required. The disclosure provides a convenient way to supply these different concentration gases to the spectrometer by mixing pure $CO_2$ with $CO_2$-free air (also termed zero air), or other $CO_2$-free gas. As reference gases for isotope analysis gases are typically expensive and air-$CO_2$ mixtures require large gas cylinders it is an advantage to use pure $CO_2$ as a reference gas instead of a pre-mixture as described in the prior art. Pure $CO_2$ with various certified isotope values as reference for isotope ratio analysis is commercially available and 1 kg $CO_2$ may last for the whole instrument lifetime. The dilution is performed to give the required 200-4,000 (such as 200-3,500) ppm $CO_2$ in air (or in $N_2$). Further advantageously, $CO_2$-free air can either be produced in the field using a $CO_2$ absorber or delivered in gas tanks. The $CO_2$ may be supplied, for example, in standard 13 liter (L) containers or in 1 L (low pressure) containers. The latter may be conveniently shipped or mailed with standard air freight. It is possible to produce more than 15,000 $m^3$ of gas mixture at 350 ppm $CO_2$ in air using one commercial 13 L gas cylinder of $CO_2$ by mixing it with $CO_2$-free air. Thus, the working lifetime of a 13 L $CO_2$ gas cylinder in various embodiments may be several years. To have a better stability of the gas flow and avoid possible isotope fractionation by a flow controller the gas inlet system is used. In contrast to the prior art, the flow of $CO_2$-free air (zero air) is controlled by a flow control means (e.g. flow controller or a proportional valve) and instead the $CO_2$ flow is kept constant. For higher dynamic range and flow matching the dilution can be done in two steps as described in more detail below.

Another advantage of using pure $CO_2$ (or other pure reference gases) as reference gas, is that this makes it easy to switch to another carrier gas (for example to use helium, argon or nitrogen instead of zero air). In a laser spectrometer, the absorption spectrum of an analyte (sample) gas is also influenced by the surrounding gases. Therefore, the main components of the gas mixture should ideally be the same or similar for the reference gas and the sample gas. In the system according to the present disclosure, it is possible to switch the carrier gas (e.g. to be the same or similar to the gas surrounding the sample gas) without changing the valuable reference gas.

Figure 2:
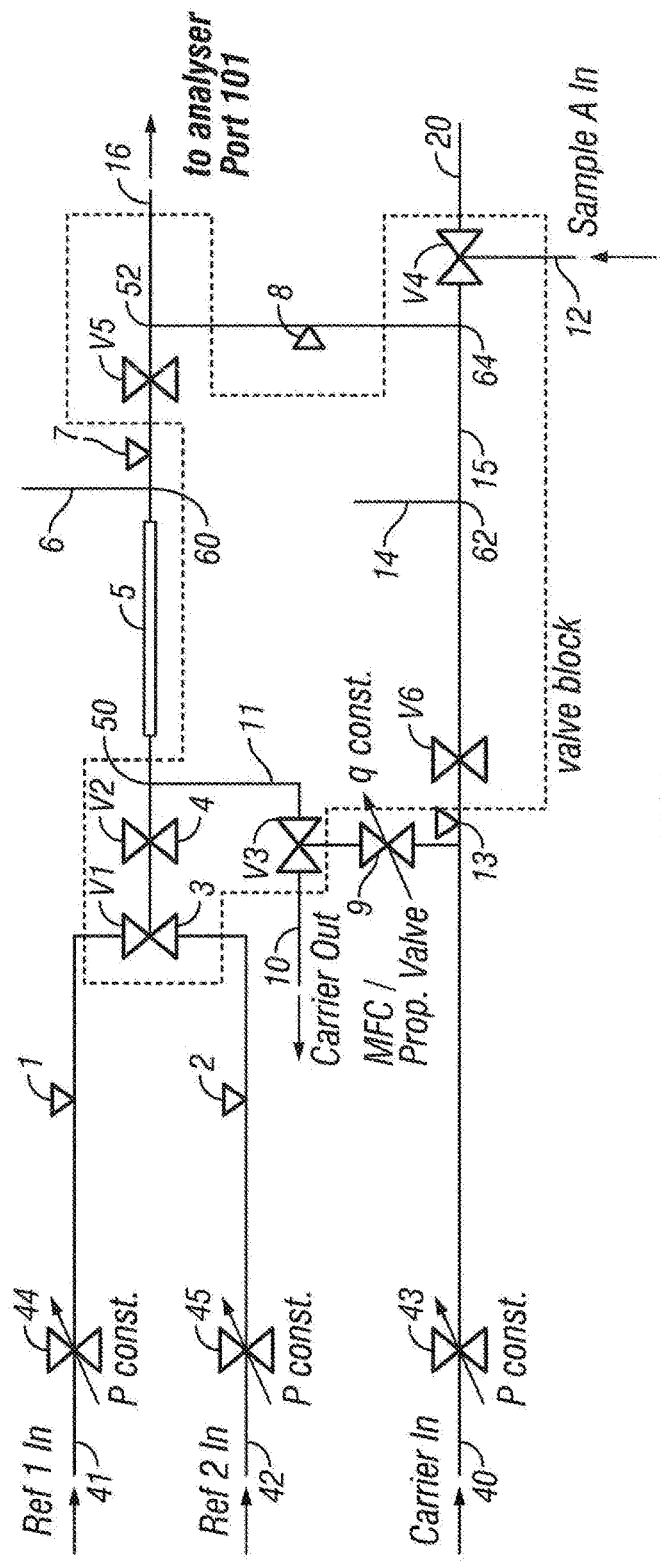
FIG. 2 shows a schematic layout of a gas inlet and referencing system in accordance with the present disclosure.

Referring to FIG. 2, there is shown a gas inlet and referencing system according to the disclosure. Firstly, it is noted how the system connects with the spectrometer shown in FIG. 1. The exit line (16) of the system shown in FIG. 2 connects with port (101) of the gas inlet system shown in FIG. 1. Thus, gases exiting from the system shown in FIG. 2 enter the spectrometer shown in FIG. 1 for isotope ratio measurement. The system is configured to be able to deliver sample gas and reference gas to the optical laser spectrometer.

Figure 3:
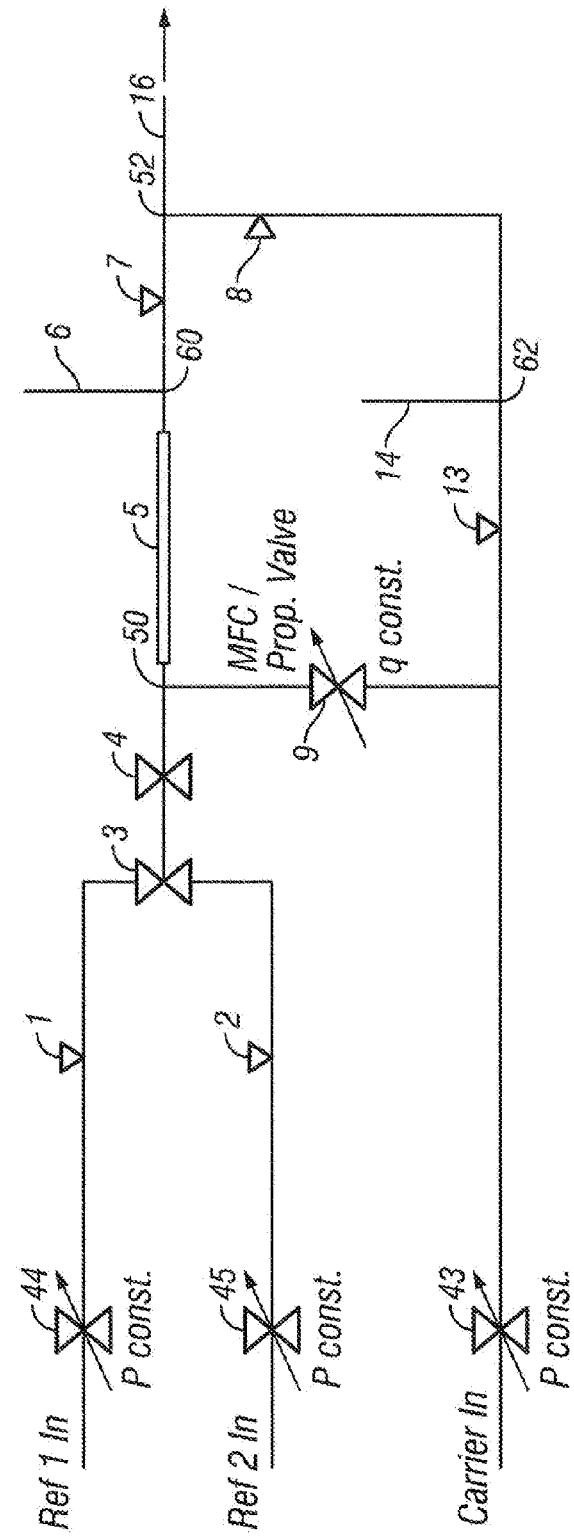
FIG. 3 shows a schematic layout of the referencing section of the system shown in FIG. 2.

Supplies of two pure $CO_2$ reference gases (ref 1 and ref 2) are provided (41, 42). The isotope ratio ($^{13}C/^{12}C$ and/or $^{18}O/^{16}O$) of each $CO_2$ supply is known. The flow of each supply of $CO_2$ is controlled by a respective valve (44, 45), which are constant pressure valves, and a respective flow restriction (1, 2) on the supply lines. The two valves V1 and V2 (3, 4) on the reference gas line allow switching between the two reference gases as well as shutting them both off from the rest of the system to save reference gas. A supply of a carrier gas, which is $CO_2$-free air, is also provided (40), the flow of which is controlled by a respective valve (43), which is a constant pressure valve. For simplicity, FIG. 3 shows the flow scheme of the referencing section of the inlet system alone.

To avoid fractionation of the $CO_2$, a constant flow of $CO_2$ of 400 μl/s (24 ml/min) from a selected one of the $CO_2$ reference supplies is mixed into a variable flow of $CO_2$-free air (or other carrier gas) (flow rate 3 to 100 ml/min) using a mass flow controller or a proportional valve (9) on the carrier gas line. The mass flow controller or a proportional valve (9) is in this embodiment computer controlled (such as most or all valves shown in the system are computer controlled). That is, the $CO_2$ is not subject to variable mass flow control, thus avoiding fractionation, but rather it is the $CO_2$-free air that is dynamically flow controlled. The gases first mix at T-junction (50), which is a first mixing junction. The gases further mix downstream inside a mixing zone (5), which is a tube with 0.8 mm inner diameter and a minimum length of 75 mm to get a homogeneous mixture of the two gases. The flow restrictions (1, 2) and constant input pressure valves (44, 45) of the $CO_2$ references define the constant $CO_2$ flow into the mixing zone (5). The $CO_2$ concentration of this resultant pre-mixture is designed to be in the range from 4,000 ppm to 13,000 ppm. The mixing zone (5) is necessary to ensure that the $CO_2$ and the zero air are thoroughly mixed. As the flow rate here can be larger than 100 ml/min, the residence time of the gas in the mixing zone (5) may be very short. With such flow rates, for a 75 mm length and 1 mm width (i.e. internal diameter(id)) of the mixing zone, the residence time would be only 35 msec. Under these conditions the flow is still laminar and mixing occurs by diffusion with nearly no concentration gradient across the capillary. In view of such considerations, the mixing zone can be at least 75 mm in length and at least 0.8 mm id.

Whilst gas mixing can occur where the mixing zone is a straight mixing tube between the two T-junctions with constant cross section along its length, it is desirable to provide features to improve mixing in the mixing zone.

In various embodiments, the dimensionless number $(D*l/j)>0.67$
Where (in SI units)
D: (Inter)Diffusion coefficient of the analyte gas in the carrier gas ($m^2/s$),
l: length of the mixing tube (m),
j: flow in this tube ($m^3/s$).

Thus, it is ensured that the concentration at the end of the mixing tube differs at no point across the area cross section more than 1% from the mean concentration. If $(D*l/j)>0.94$ the concentration at the end of the mixing tube differs at no point across the area cross section more than 1 per mil from the mean concentration. Mixing can be assisted by one or more of the following measures:
  i. Providing an angle (e.g. a 90° angle) along the length between the two T-junctions
  ii. Bending, e.g. including knotting or meandering, of the mixing tube
  iii. Periodically or arbitrarily changing the area cross section along the tube
  iv. Using a carrier gas with a higher interdiffusion coefficient
  v. Heating the tube
  vi. Modifying the T-junctions so that the addition of the reference gas is in the middle of the cross section of the mixing tube.

The $CO_2$ pre-mixture is further mixed with more $CO_2$-free air (carrier gas) at a second T-junction or flow splitter (52). This is thus a second mixing junction. A second dilution of the reference flows is set to an appropriate fixed ratio (for example 1:30). The flow to the second mixing T-junction is defined by two flow restrictions (7, 8), which in this embodiment ensure a ratio between the pre-mixture and $CO_2$-free air of 1:30. That is, flow restriction (7) restricts flow of pre-mixture and flow restriction (8) restricts flow of carrier gas. The flow of the pre-mixture is defined by the flow controller (9) and is always higher than 1/30 of the gas flow into the laser spectrometer. This two stage dilution can be due to limitations of the dynamic range of down-mixing in practice. The progressive linearity calibration of the concentration dependence is then performed by use of flow controller (9).

The input pressure of both restrictions (7) and (8) is kept equal at approximately atmospheric pressure by two openings in the form of open tubes or capillaries (6, 14) on the pre-mixture exit line and the carrier gas line respectively. Thus, the rest of the pre-mixture is blown out of the opening (6) positioned after (downstream of) the mixing zone, between the mixing zone (5) and the flow restriction (7). The flow of the $CO_2$-free air towards the second mixing split is defined by a flow restriction (13) and the constant pressure in the supply (43) of the $CO_2$-free air. The gas flow at the restriction (13) is always higher than the gas flow to the laser spectrometer. The differential amount of $CO_2$-free air carrier gas is blown out of an opening (14) on the carrier gas line.

The openings (6, 14) are situated on T (or Y) piece connections (60, 62). The openings (6, 14) are dimensioned such that the gas velocity is always higher than the diffusion velocity of $CO_2$ in air to avoid contaminations of the reference gases. From the above it can be seen that the reference gas flows are very low and should not be dynamically regulated or actively controlled (i.e. valves 1 and 2 (at locations 3, 4) are typically on/off valves). Thus, the reference gas flows from the reference gas supplies, via valves 1 and 2, are not changed when changing the $CO_2$ concentration in the spectrometer. Instead, a first dilution of the reference gas flow is dynamically regulated by controlling flow of the zero air (using computer controlled valve (9)). Moreover, the costly conventional open split arrangement is replaced by a simple T (or Y) connection placed after the mixing zone. The opening (6) on the T connection (60) is a length of capillary, and the length of the opening is calculated to balance diffusion versus flow to avoid fractionation and thus change of the isotope ratio of the reference at the open split. The capillary of the opening (6) should not offer a marked restriction, so that the pressure at the T connection (60) is always very close to the atmospheric pressure. This means that the flow rates in this capillary will be not too high. The pressure drop across the opening (6) can be arranged to be 250 mbar or less, especially 50 mbar or less. On the other hand, the flow speed is controlled to be high enough to make sure that back-diffusion of the reference gas against the carrier gas flow is low enough, otherwise it could lead to fractionation (altering of the isotope ratio). An example of dimensions for the capillary of the opening (6) is: 1 mm internal diameter(id), 1 cm length. Generally similar considerations apply to the opening (14).

A first example of parameters for the reference opening is:
i. Reference: $CO_2$ in zero air
ii. Minimum flow through open split (6) capillary: 0.5 ml/min (i.e. a flow of at least 0.5 ml/min)
iii. Open split capillary diameter: 1 mm
iv. Minimum flow to open split: 1 ml/min (i.e. a flow of at least 1 ml/min)
v. Loss of flow through open split<$1/1000$ of input flow
vi. Fractionation<0.3 per meg on mass 46
This fractionation is achieved for all lengths>1 cm.
A second example of parameters for the reference opening is:
i. Reference: $CO_2$ in zero air
ii. Minimum flow through open split capillary: 0.5 ml/min
iii. Open split capillary diameter: 2 mm
iv. Minimum flow to open split: 1 ml/min
v. Loss of flow through open split<$1/1000$ of input flow
vi. Fractionation<0.5 per meg on mass 46
This fractionation is achieved for all lengths>3.7 cm.

Figure 4:
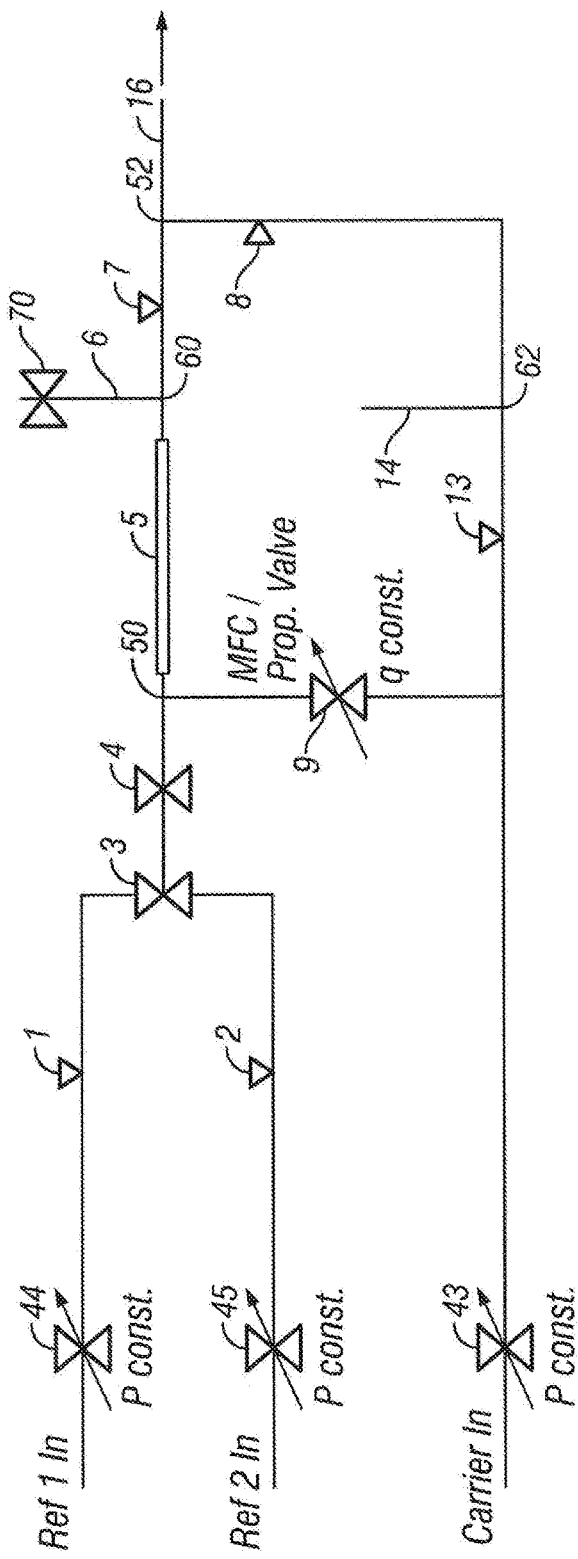
FIG. 4 shows a schematic layout of the referencing section as shown in FIG. 3 with optional valve for closure of an opening to atmosphere.
Figure 5:
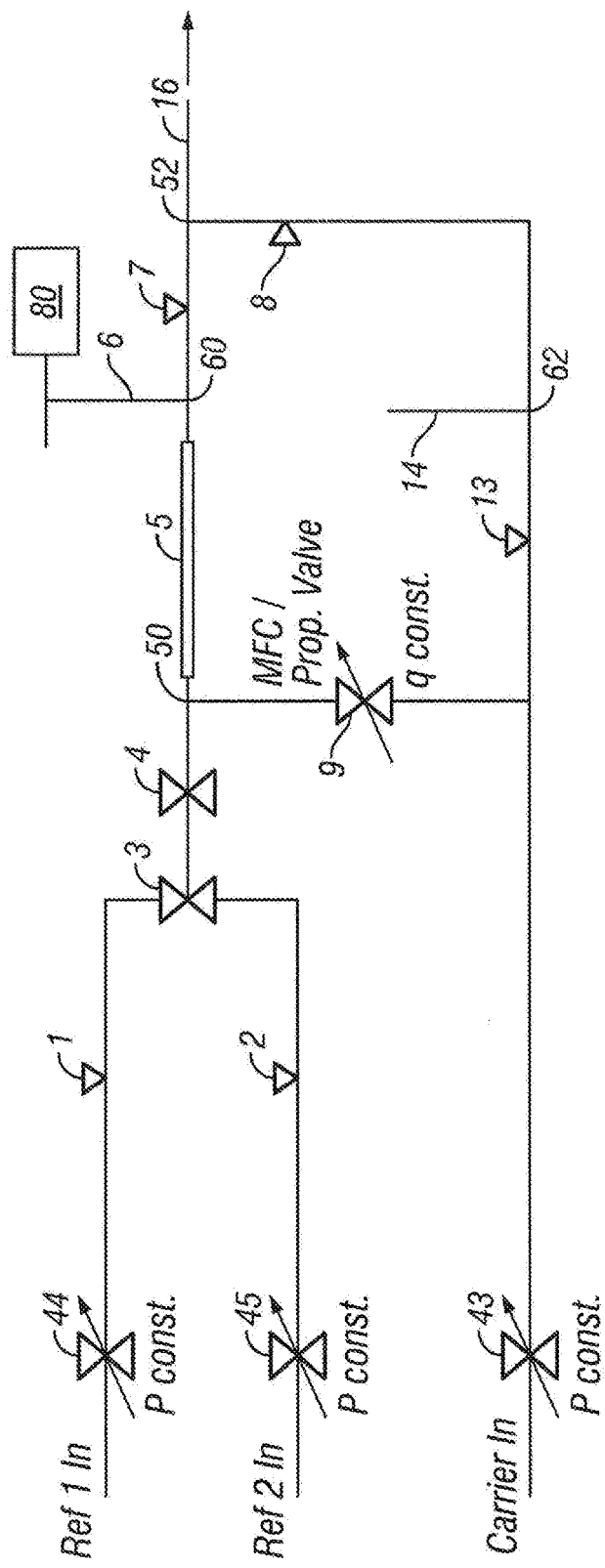
FIG. 5 shows a schematic layout of the referencing section as shown in FIG. 3 with optional zero air supply in an opening to atmosphere.

In some situations, it might be convenient to block opening (6) against diffusion of contaminating components from the air (e.g. humidity), such as when the reference gas is switched off and when there is no carrier gas flow through the mass flow controller (9). This can be done in two ways for example: the opening can be blocked by a valve (70) as shown in FIG. 4, or a zero air flow (80) can protect the opening (6) from being in contact with the contamination as shown in FIG. 5. It will be appreciated that opening (14) likewise can optionally be provided with a similar blocking valve or zero air flow.

The referencing system is designed to allow dilution of the supplied gases by mixing different gases with each other to change concentrations of the desired gas species (e.g. $CO_2$ in zero air). It can be seen that by varying the flow of the carrier gas using mass flow controller (9), the concentration of $CO_2$ reference gas in the $CO_2$-free carrier gas can be varied. The referencing system allows any concentration of the $CO_2$ for linearity calibration in the measurement range of the spectrometer from 100-4,000 ppm, such as 200-3,500 ppm. In this way, isotope ratio measurements can be taken in the spectrometer at a plurality of different $CO_2$ concentrations to enable a concentration dependence of the isotope ratio measurement to be determined.

An exit line (16) takes the flow from the mixing zone into the optical laser spectrometer after the second stage of dilution. The output flow into the optical laser spectrometer is defined by the spectrometer itself and is ideally 80 ml/min. The pressure at the outlet (16) that interfaces to the spectrometer is designed to be around atmospheric pressure.

In the described embodiments, it is possible to switch between the two reference gases with different isotopic ratios. Therefore, the same reference gases used for determination of the concentration dependence (linearity calibration) can be used to perform a delta scale calibration. As the reference gases can be diluted to any concentration, the delta scale calibration can be done at any concentrations or even at more than one concentration to achieve a high accuracy over a wide range. The measured sample should be close to the concentration of the reference gases to avoid linearity effects of the analyzer. For ambient (air) applications, the described setup enables the user also to dilute or mix the reference into the concentration range of the sample to avoid linearity effects of the analyzer. It is also possible to measure the sample with unknown concentration first and afterwards measure the reference with a similar concentration as the sample.

In addition to the referencing system described above, the gas inlet system shown in FIG. 2 further comprises a sample inlet system for introducing a sample gas (i.e. of unknown isotope ratio and/or concentration) into the spectrometer. For simplicity, the sample inlet part of the system in FIG. 2 is shown alone in FIG. 6 and described in more detail below. Sample gas from the sample inlet system (FIG. 6) and reference gas from the referencing system (i.e. shown in FIGS. 3 to 5) can be periodically supplied to the measurement cell. In this way, the software controlled valve switching allows intermittent injection of reference gas for quality assurance and/or calibration of the spectrometer.

Figure 6:
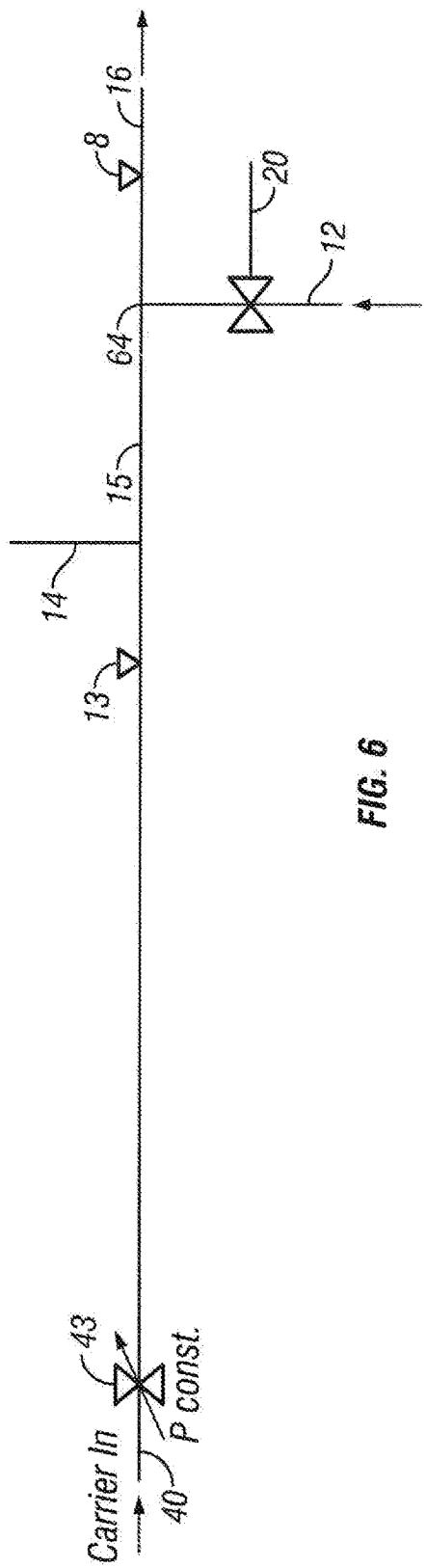
FIG. 6 shows a schematic layout of the sample inlet section of the system shown in FIG. 2.

In the arrangement shown in FIG. 6, the flow of $CO_2$-free air, which is defined by a fixed flow restriction (13), is mixed with a $CO_2$ sample flow coming from a sample inlet port (12) to which is connected a supply of sample gas ($CO_2$). In this embodiment, the supply of $CO_2$-free air for the sample flow is the same supply (40) as used for dilution of the reference gases in the referencing system described above.

The sample inlet system according to the disclosure ensures 100% sample transfer from the sample input port ((12) in FIG. 6) to the laser spectrometer (16). A constant flow to the laser spectrometer is ensured by filling the differential volume between the sample flow and the flow to the laser spectrometer with a carrier or dilution gas, which in this case is $CO_2$-free air (zero air). No sample is wasted and the concentration of $CO_2$ in the gas flow to the laser spectrometer is kept constant and in the optimal range. In some embodiments, using a variable flow of $CO_2$-free air, any sample vials with a variable $CO_2$ concentration over time can be flushed out through the sample inlet port to ensure the concentration of $CO_2$ in the gas flow to the laser spectrometer is kept constant and in the optimal range.

The samples are frequently only available in minute quantities. Thus, the sample inlet system must ensure that little or no sample is lost. This is achieved in the embodiment shown by means of the open split in the form of the opening (14) constructed with the T-junction technology as described above. The sample from inlet (12) is introduced via its gas line into the stream of the carrier gas after (i.e. downstream of) the open split (14) at sample introduction point (64), which is also termed herein an analyte-carrier junction. Such sample introduction point is also a T-junction. This is in contrast to the prior art open splits where sample is introduced into a carrier or dilution gas at the open split itself such that significant sample loss occurs. The T-junction sample introduction and separate T-junction opening to atmosphere not only preserve the sample in the carrier without sample loss but the T-junction construction is simpler to manufacture and more robust in use.

It is required that the sample flow (12) must not be identical or very close to the flow at the output (16). As long as the sample flow is lower than the flow at the output (16) into the laser spectrometer, the flow between the opening (14) and the sample introduction point (64) is always directed towards the laser spectrometer (and if the sample flow is sufficiently lower than the flow at the output (16) the $CO_2$ concentration at (14) is close to zero). Diffusion of $CO_2$ sample backwards is thereby prevented by the relative magnitudes of the flow rates. This guarantees a 100% sample transfer from the sample inlet port (12) into the laser spectrometer. The sample, however, is diluted and the dilution factor is defined by the sample flow rate. That is, when the sample flow is lower than the flow at the output (16), the concentration of sample at (16) is lower than that of the sample inlet flow (12). The difference between the flow to the laser spectrometer (16) and the sample input flow (12) is balanced by the $CO_2$-free air at (13). The excess $CO_2$-free air is blown out through the opening (14) on the carrier gas line. If the sample inlet flow (12) is higher than the flow at the output (16), which is also a workable embodiment, the concentration at opening (14) represents a mixture of the concentration at sample inlet (12) and that at the supply of $CO_2$-free air (40) (which is zero concentration by definition). In all cases, the $CO_2$ isotope ratios at (12), (14) and (16) are substantially identical, which is significant.

An additional three port valve (valve V4) in the sample inlet (12) is used to be able to flush the sample line through inlet port (20). In operation of the sample inlet system, the carrier gas flow is only provided through restriction (13), not through variable flow controller (9).

The opening (14) opens to atmosphere in the same way as opening (6) described above, and the distance between the T-junction with the opening (14) and the T-junction with the sample introduction point (64) is selected such that substantially no back-diffusion into the opening (14) occurs. In particular, the flow rate and line length and cross section are such that substantially no back-diffusion occurs. Thus, only the inexpensive dilution gas is wasted. The considerations for the line (15) between both T-junctions are the similar to the reference gas split. The flow into the analyzer is relatively high at typically 100 ml/min. In various embodiments, the minimum flow to the open split (opening (14)) should be 10 ml/min. Furthermore, it should be ensured that the flow through the open capillary (14) is always at least 0.5 ml/min. In various embodiments, a length of the open capillary (14) is at least 5 mm or 6 mm, such as at least 10 mm, and an internal diameter can be at least 1.0 mm, e.g. 1.3 mm. The loss of flow through the open split is then typically<1/1000 of the input flow and there is little or no fractionation effect. The pressure drop across the opening (14) can be arranged to be 250 mbar or less, especially 50 mbar or less.

An example of parameters for the sample inlet opening (14) is:
  i. Sample: $CO_2$ gas in zero air (e.g. dilution of sample: carrier=1:1 to 1:0).
  ii. Minimum flow through open split capillary: 0.5 ml/min (i.e. the flow should be at least 0.5 ml/min)
  iii. Open split capillary diameter: 1 mm
  iv. Minimum flow to open split: 10 ml/min (i.e. the flow should be at least 10 ml/min)
  v. Loss of flow through open split <1/1000 of input flow
  vi. Fractionation<0.3 per meg on mass 46

This fractionation is achieved for all lengths>6 mm.

In the case of interfacing a gas chromatography (GC) system to an isotope ratio mass spectrometer (IRMS), an example of parameters for the inlet opening is:
  i. Gas: Hydrogen in He
  ii. Minimum flow through open split capillary: 0.5 ml/min
  iii. Open split capillary diameter: 0.5 mm
  iv. Minimum GC flow to open split: 0.8 ml/min
  v. Loss of flow through open split<1/100 of input flow
  vi. Fractionation<60 per meg (0.06 per mil) for the $H_2$/HD ratio This fractionation is achieved for all lengths>1.52 cm.

The gas line downstream of the sample introduction point is a mixing zone for the sample $CO_2$ in air and can be subject to similar considerations of design parameters as the mixing zone (5) of the reference section described above. Moreover, it can be improved as a mixing zone by any of the measures described above in relation to the mixing zone (5) of the reference section of the system.

Figure 7:
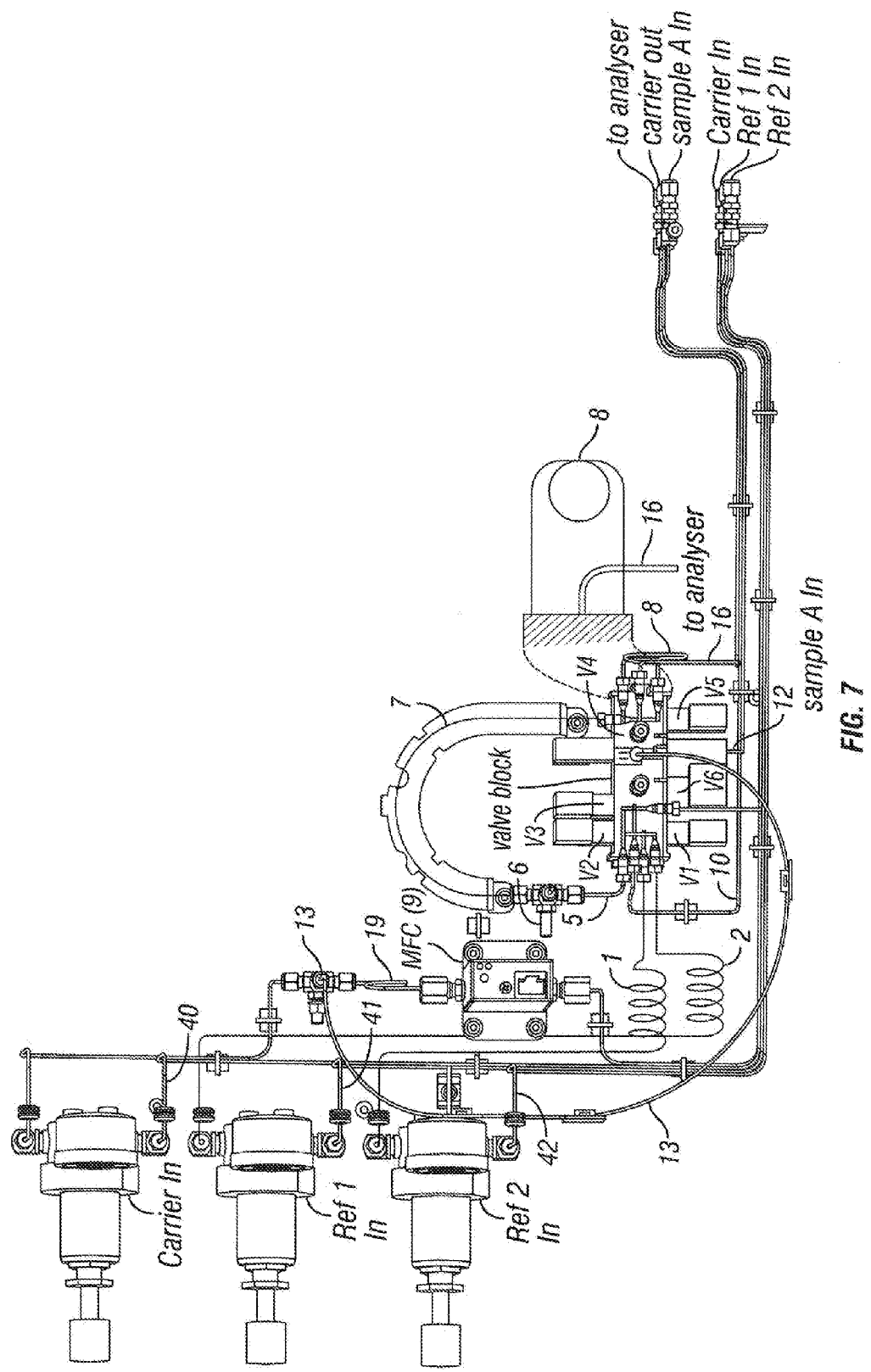
FIG. 7 shows an embodiment of a system in accordance with the schematic layout of FIG. 2.
Figure 8:
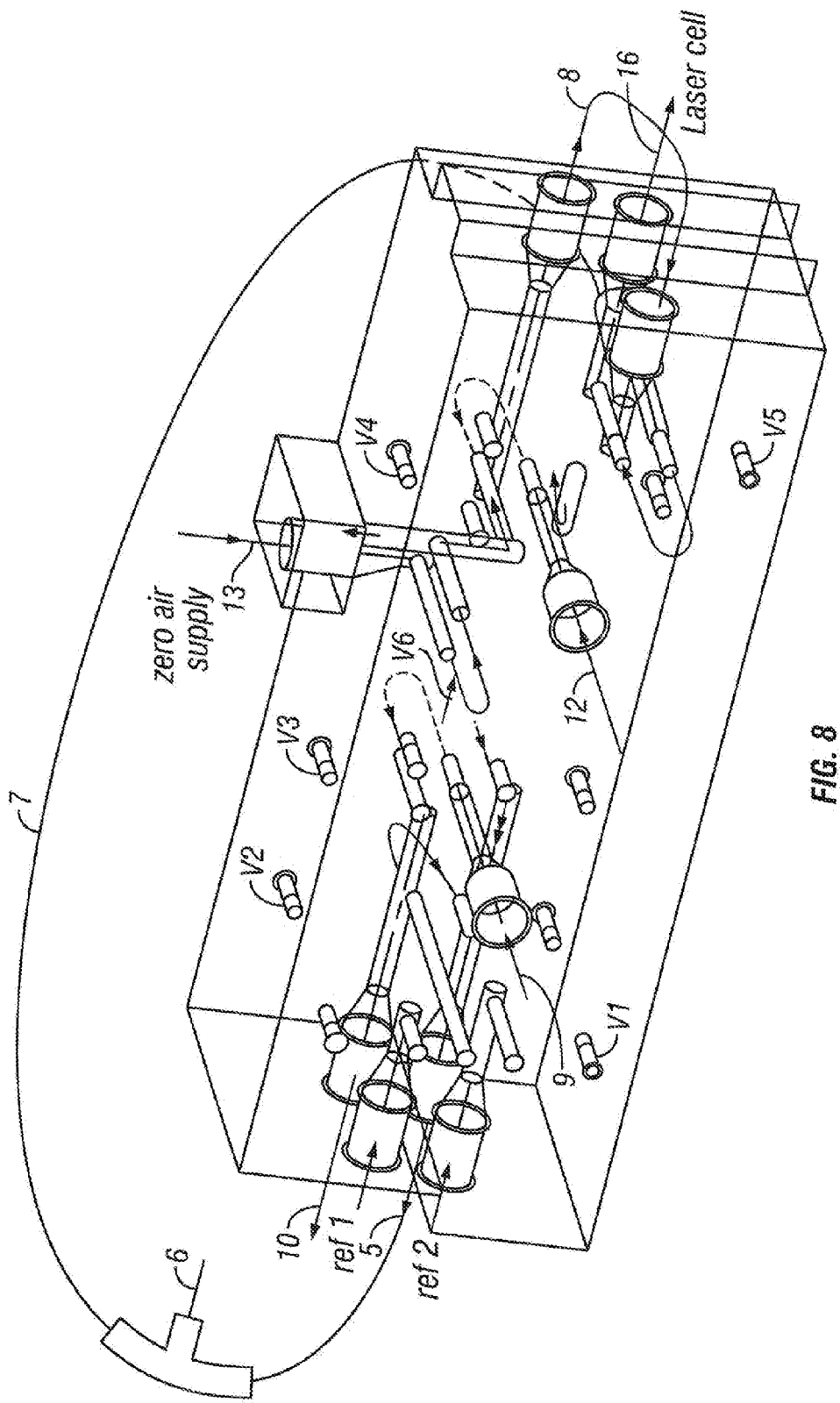
FIG. 8 shows an embodiment of a machined valve block for use in a system as shown in FIG. 7.

The system can be realized as a compact, robust system. One such embodiment is shown in FIG. 7, where the same reference numerals are used to denote the same components as shown in FIG. 2. A part of the system is provided in a machined metal block, which is denoted as the valve block and indicated schematically by the dotted line in FIG. 2 with the block itself shown in FIG. 7. In the shown embodiment, the valve block is made of metal, but a suitable polymer (e.g. PEEK) or other suitable material could be used to make it as well. It is also possible to make the block comprising of several multilayers bonded together with buried channels. Valves V1-V6 are housed in the valve block. Valves V1 (3/2) and V2 (2/2) are for switching the entry of the reference gases (41, 42) into the system as described above; valve V3 (3/2) is for switching flow of the carrier gas from the mass flow controller (9) to direct it to the mixing zone (5), or to a separate outlet (10); valve V4 (3/2) is for switching the flow of sample gas from the sample inlet (12) into the carrier gas and the spectrometer; valve V5 (2/2) is for switching flow of the diluted reference gas into the analyzer from the mixing zone (5); and valve V6 (2/2) is for switching flow of the carrier gas along the line that is not controlled by the mass flow controller. The valve block structure is shown in more detail in FIG. 8, where the same reference numerals are again used. The positions of the valves in the block and some of the connecting flow channels are shown. The channels are typically drilled in the block. The dimensions indicated in FIG. 8 are in mm. The flow restrictions in the system, such as restrictions (1, 2, 7, 8 and 13) can each be provided as a metal capillary or as metal capillary having a crimp and the openings to atmosphere (6, 14) are provided simply as T junctions using capillaries. Thus, the system can be assembled largely from stock components.

It can be seen from the description herein that the gas inlet system is a compact device to deliver sample and reference gas to an isotope ratio analyzer, especially an optical spectrometer. The main target is to allow comparative measurement of isotope ratios of a sample and one or more reference gases. The concentrations of the sample and reference gas should be matched to one another and to the optimum concentration range suitable for the isotope ratio analyzer used. In embodiments of the disclosure comprise two functional units: a reference section and a sample inlet section. Various embodiments are designed to allow dilution of the supplied gases by mixing different gases with each other to change concentrations of the desired gas species (e.g. $CO_2$ in air). Software controlled valve switching allows intermittent injection of reference gas for quality assurance and/or calibration of the spectrometer. The gas inlet system with the analyzer to which it is interfaced can be dedicated to analyze the isotope ratio of $^{13}C/^{12}C$ and/or $^{18}O/^{16}O$ from $CO_2$ in air or other carrier gases (e.g. $N_2$), or it can be designed to analyze these or other isotope ratios of other gases.

Using the system shown in the Figures, an isotope ratio of a sample may be measured and corrected for concentration dependence of the spectrometer. The concentration dependence may be determined by selecting a reference gas (e.g. Ref 1 (41)), which has a first known isotope ratio, and measuring in the laser cell the isotope ratio of the reference gas with the first known isotope ratio at a plurality of concentrations in a carrier gas, wherein the concentrations can be varied as described above by using the referencing system shown in FIGS. 2 and 3. From the measurements at the plurality of concentrations, a concentration dependence of the isotope ratio measurements of the reference gas is determined (e.g. from a plot of isotope ratio against concentration). A sample gas of unknown isotope ratio and unknown concentration may be admitted into the system using the sample inlet system shown in FIGS. 2 and 6 and its isotope ratio and concentration measured in the laser cell. The isotope ratio measurement of the sample gas may be corrected by the determined concentration dependence.

Furthermore, using the system shown in the Figures, the isotope ratio of the sample may be corrected by an isotope ratio calibration (or delta scale contraction) of the spectrometer. This method includes selecting the reference gas (e.g. Ref 2 (42)), which has a second known isotope ratio, and measuring in the laser cell the isotope ratio of the reference gas with the second known isotope ratio, such as at one or more concentrations in the carrier gas that lie within the range of measured concentrations of the reference gas with the first known isotope (Ref 1). An isotope ratio calibration can then be determined from the measured isotope ratios of the reference gas with the first and second known isotope ratios and the measured isotope ratio of the sample gas can be further corrected by the determined isotope ratio calibration.

As used herein, including in the claims, unless the context indicates otherwise, singular forms of the terms herein are to be construed as including the plural form and vice versa.

Throughout the description and claims of this specification, the words "comprise", "including", "having" and "contain" and variations of the words, for example "comprising" and "comprises" etc., mean "including but not limited to", and are not intended to (and do not) exclude other components.

It will be appreciated that variations to the foregoing embodiments can be made while still falling within the scope of the disclosure. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example" and like language) provided herein, is intended merely to better illustrate embodiments of the disclosure and does not indicate a limitation on the scope of the disclosure unless otherwise claimed. No language in the specification should be construed as indicating any non-claimed element as essential to the practice of the invention.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the features of the disclosure can be applicable to all aspects of the disclosure and may be used in any combination. Likewise, features described in non-essential combinations may be used separately (not in combination).

What is claimed is:

1. A gas inlet system for introducing gas into an isotope ratio analyzer,
    the gas inlet system including a reference system comprising:
    a first supply of a reference gas having a first known isotope ratio;
    a supply of a carrier gas,
    wherein the supplies of reference gas and carrier gas are each connected by respective reference and carrier gas lines to a first mixing junction where the reference gas and carrier gas combine;
    a mixing zone connected downstream of the first mixing junction wherein the combined reference gas and carrier gas mix together;
    an exit line for transporting the mixed gas from the mixing zone to the isotope ratio analyzer;
    a second mixing junction on the exit line from the mixing zone for mixing further carrier gas with the already mixed gas, the further carrier gas being supplied to the second mixing zone via a second carrier gas line; and
    an opening on the exit line, wherein the opening is downstream of the mixing zone.

2. A gas inlet system according to claim 1, the reference system further comprising a second supply of a reference gas having a second known isotope ratio, wherein the first and second supplies of reference gas may be each independently connected to the first mixing junction for mixing with the carrier gas.

3. A gas inlet system according to claim 1 wherein the reference gas is a substantially pure gas and the carrier gas is substantially free from the reference gas.

4. A gas inlet system according to claim 3 wherein the reference gas is $CO_2$ and the carrier gas is $CO_2$-free air or $CO_2$-free nitrogen.

5. A gas inlet system according to claim 1 wherein the carrier gas flow to the first mixing junction is dynamically controllable by flow control means.

6. A gas inlet system according to claim 5 wherein the flow control means comprises a mass flow controller or proportional valve.

7. A gas inlet system according to claim 5 wherein the flow control means comprises at least one automatic or manual pressure regulator combined with at least one flow restriction downstream of the pressure regulator.

8. A gas inlet system according to claim 1 wherein the opening is in the form of an open capillary that is at least 0.5 mm in internal diameter and at least 5 mm in length.

9. A gas inlet system according to claim 8 wherein the flow rate through the open capillary is at least 0.5 ml/min.

10. A gas inlet system according to claim 1 wherein the mixing zone is at least 75 mm in length and at least 0.8 mm internal diameter.

11. A gas inlet system according to claim 1 wherein the mixing zone includes one or more bends and/or includes an angle along its length.

12. A gas inlet system according to claim 1 wherein the second mixing junction is downstream of the opening on the exit line.

13. A gas inlet system according to claim 1 wherein the carrier gas supplied to the second mixing junction is from the same supply of carrier gas that supplies the first mixing junction.

14. A gas inlet system according to claim 1 wherein the carrier gas supplied to the second mixing junction is not dynamically controllable.

15. A gas inlet system according to claim 1 wherein the exit line from the mixing zone has a flow restriction upstream of the second mixing junction but situated downstream of the opening junction and the second carrier gas line also has a flow restriction upstream of the second mixing junction.

16. A gas inlet system according to claim 1 wherein the mixed gas that enters the analyzer comprises a $CO_2$ in air or $CO_2$ in nitrogen concentration in the range between about 200-1500 ppm.

17. A gas inlet system according to claim 1 wherein each mixing junction is a T-junction.

18. A gas inlet system according to claim 1 wherein the opening on the exit line is provided at a junction that is a T-junction.

19. A gas inlet system according to claim 1 wherein one or more portions of the gas lines are provided in a machined block.

20. A gas inlet system according to claim 1 wherein the isotope ratio analyzer is an isotope ratio mass spectrometer or an isotope ratio optical spectrometer.

21. A gas inlet system according to claim 1 wherein the isotope ratio analyzer is for determination of a concentration dependence of an isotope ratio measurement and/or determination of an isotope ratio dependence of the isotope ratio measurement.

* * * * *